(12) United States Patent
Cantillon et al.

(10) Patent No.: US 12,763,175 B2
(45) Date of Patent: Oct. 13, 2026

(54) SYSTEMS AND METHODS FOR REMOTE MONITORING OF NON-CRITICALLY ILL HOSPITALIZED PATIENTS

(71) Applicant: THE CLEVELAND CLINIC FOUNDATION, Cleveland, OH (US)

(72) Inventors: Daniel J. Cantillon, Hudson, OH (US); Molly Loy, Westlake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 505 days.

(21) Appl. No.: 18/094,301

(22) Filed: Jan. 6, 2023

(65) Prior Publication Data

US 2023/0290454 A1 Sep. 14, 2023

Related U.S. Application Data

(63) Continuation of application No. 15/432,059, filed on Feb. 14, 2017, now Pat. No. 11,557,383.

(Continued)

(51) Int. Cl.

*G16H 10/60* (2018.01)
*G16H 40/63* (2018.01)

(Continued)

(52) U.S. Cl.

CPC ............. *G16H 10/60* (2018.01); *G16H 40/63* (2018.01); *G16H 40/67* (2018.01); *G16H 50/30* (2018.01)

(58) Field of Classification Search

CPC ........ G16H 10/60; G16H 40/63; G16H 40/67; G16H 50/30

See application file for complete search history.

(56) References Cited

U.S. PATENT DOCUMENTS

| | | | | |
|---|---|---|---|---|
| 6,110,384 | A | 8/2000 | Goux et al. | |
| 2002/0095077 | A1* | 7/2002 | Swedlow ............ | A61B 5/1495 600/323 |

(Continued)

FOREIGN PATENT DOCUMENTS

| | | | |
|---|---|---|---|
| GB | 2485243 | A | 5/2012 |
| WO | 2006031186 | A | 3/2006 |
| WO | 2008087470 | A1 | 7/2008 |

OTHER PUBLICATIONS

Communication pursuant to Article 94(3) EPC regarding examination of Application No. 17706390.6-1122, dated Mar. 1, 2025, 13 pages.

(Continued)

*Primary Examiner* — Peter H Choi

(74) *Attorney, Agent, or Firm* — Tarolli, Sundheim, Covell & Tummino LLP

(57) ABSTRACT

Described herein is a system for remote monitoring of non-critically ill hospitalized patients. The system can include a graphical user interface displaying a representation of the patient census. Each patient is represented by a graphic showing a clinical status, with an underlying expanded view of various parameters. The system can also include a non-transitory memory storing computer executable instructions and a processor configured to execute the computer executable instructions. Upon execution, the computer executable instructions can at least: receive a data stream associated with a non-critically ill hospitalized patient; determine a risk score associated with the non-critically ill hospitalized patient based on data associated with the alarm notification, wherein the risk score represents a probability of the non-critically ill hospitalized patient (Continued)

developing an actionable clinical event; and rearrange the plurality of graphical representations on the GUI based on the risk score.

20 Claims, 7 Drawing Sheets

Related U.S. Application Data

(60) Provisional application No. 62/296,121, filed on Feb. 17, 2016.

(51) Int. Cl.
*G16H 40/67* (2018.01)
*G16H 50/30* (2018.01)

(56) References Cited

U.S. PATENT DOCUMENTS

2004/0225201 A1 11/2004 Mcnair
2010/0131434 A1* 5/2010 Magent .................. G16H 10/60 706/14
2011/0169644 A1* 7/2011 Muhsin ................ G08B 25/008 340/573.1
2013/0027411 A1* 1/2013 Hebler ................... G16H 50/30 345/501
2013/0244892 A1* 9/2013 Adourian ........... G01N 33/6893 435/7.1
2014/0218391 A1* 8/2014 Mcconnell ........... G06Q 10/107 345/619
2014/0229880 A1* 8/2014 Aradhye ............... G06F 3/0482 715/771
2014/0366878 A1 12/2014 Baron
2017/0165040 A1* 6/2017 Wolgin ................. A61M 1/962
2018/0153478 A1* 6/2018 Johnson ............... A61B 5/7445

OTHER PUBLICATIONS

EPO Search Report regarding Application No. 17706390.6 dated Oct. 5, 2023 for Cantillon et al.
Communication pursuant to Article 94(3) EPC regarding examination of Application No. 17706390.6-1122, dated Oct. 29, 2025, 16 pages.

* cited by examiner

SYSTEMS AND METHODS FOR REMOTE MONITORING OF NON-CRITICALLY ILL HOSPITALIZED PATIENTS

RELATED APPLICATIONS

This application is a continuation of U.S. patent application Ser. No. 15/432,059, filed Feb. 14, 2017, which claims the benefit of U.S. Provisional Application No. 62/296,121, filed Feb. 17, 2016. The entirety of each application is hereby incorporated by reference for all purposes.

TECHNICAL FIELD

The present disclosure relates generally to remote monitoring of non-critically ill hospitalized patients and, more specifically, to systems and methods that employ a vendor-agnostic, risk stratified patient census with dynamic alerts to facilitate the remote monitoring of the non-critically ill hospitalized patients.

BACKGROUND

Traditionally, the responsibility for monitoring non-critically ill patients has fallen to bedside personnel. However, normal hospital activities occurring at a nursing station may distract the bedside personnel from continuous, vigilant patient monitoring. For example, busy bedside personnel may suffer from "alarm fatigue", becoming desensitized to the constant noise of various non-actionable alarms. This fatigue may result in actionable alarms requiring clinical intervention being missed.

Remote monitoring units can be a valuable tool for continuous monitoring of the physiologic condition of patients. Traditionally, these remote monitoring units employ monitoring technicians, each viewing data for a plurality of patients using monitors from a common vendor. However, these remote monitoring units also suffer from alarm fatigue, in which multiple alarms are generated simultaneously without distinction of their associated clinical relevance. The large number of non-actionable alarms can overwhelm the monitoring technicians, causing the monitoring technicians to miss an actionable alarm requiring clinical intervention. Additionally, these traditional remote monitoring units are generally unable to combine monitoring devices from different vendors efficiently or mix patients being monitored by equipment on separate networks.

SUMMARY

The present disclosure relates generally to monitoring non-critically ill hospitalized patients from a remote location, and, more specifically, to systems and methods that employ a vendor-agnostic, risk stratified patient census with dynamic alerts to combat the problem of alarm fatigue. The dynamic alerts can include the rearrangement of patients displayed on a graphical user interface (GU) according to calculated risk scores for the particular patients.

In one aspect, the present disclosure includes a system that can monitor non-critically ill patients from a remote location. The system can include a graphical user interface displaying a plurality of graphical representations, each displaying a clinical status corresponding to a unique non-critically ill hospitalized patient. Each graphical representation is expandable to a detailed view comprising parameters corresponding to the clinical status. The system can also include a non-transitory memory storing computer executable instructions; and a processor coupled to the memory and configured to execute the computer executable instructions. Upon execution the computer executable instructions can at least: receive a data stream associated with a non-critically ill hospitalized patient; determine a risk score associated with the non-critically ill hospitalized patient based on data associated with the alarm notification, wherein the risk score represents a probability of the non-critically ill hospitalized patient developing an actionable clinical event; and rearrange the plurality of graphical representations on the GUI based on the risk score, The risk score is related to the clinical status of the non-critically ill hospitalized patient. In some instances, the data stream can be related to an alarm and the risk score can indicate whether the alarm is actionable or non-actionable.

In another aspect, the present disclosure includes a method for monitoring non-critically ill hospitalized patients from a remote location. The method can include displaying, on a graphical user interface device by a system comprising a processor, a plurality of graphical representations, each graphical representation corresponding to a clinical status of a unique non-critically ill hospitalized patient; receiving, by the system, a data stream related to a non-critically ill hospitalized patient; determining, by the system, a risk score for the non-critically ill hospitalized patient based on data derived from the data stream, wherein the risk score represents a probability of the non-critically ill hospitalized patient developing an actionable clinical event; and rearranging, by the system, the display of the plurality of graphical representations on the graphical user interface based on the risk score for the non-critically ill hospitalized patient. The risk score can be applied to the associated expanded view for the patient and synchronized to the electronic medical record.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
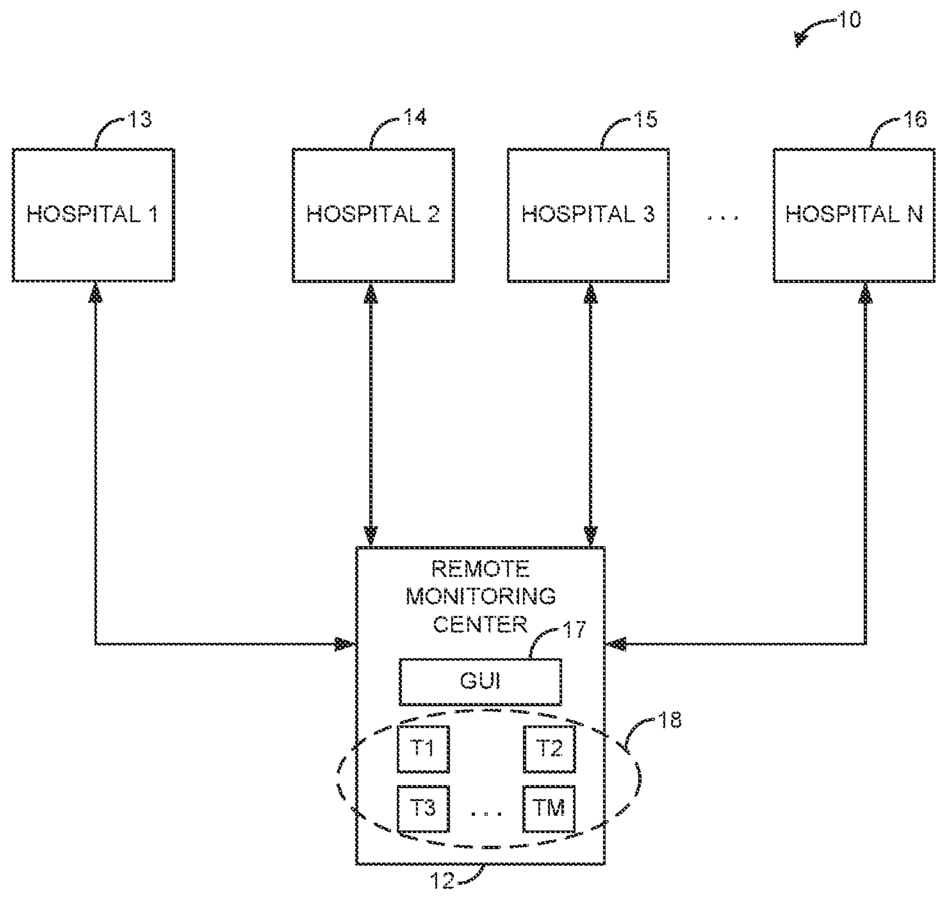
FIG. 1 is a block diagram showing a team approach for the remote monitoring of non-critically ill hospitalized patients from a plurality of different hospitals.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "remote monitoring" can refer to the observation of a disease, condition, or one or more medical parameters over time at a location remote from the patient location. For example, remote monitoring can utilize telecommunication and information technologies to provide telemetry services of remotely monitoring vital signs of non-critically ill hospitalized patients.

As used herein, a "remote" location can refer to any location in which medical practitioners therein are not delivering bedside patient care. One example of a remote location can include an off-site location from the premises of care delivery, such as an off-site central monitoring location. As another example, the remote location can be a sequestered alcove adjacent to the premises of care delivery. Thus, the term "remote" is in relation to the fixed reference of bedside patient care delivery and is independent from actual distance.

As used herein, the term "hospitalized patient" can refer to any patient receiving medical care as an inpatient or under observation as an outpatient.

As used herein, a hospitalized patient described as "non-critically ill" can refer to any hospitalized patient who is not critically ill in an intensive care unit (ICU). As an example, a non-critically ill hospitalized patient can be a hospitalized patient who has been transferred from the intensive care unit into a step-down unit. As another example, a non-critically ill hospitalized patient can be a hospitalized patient admitted to a general hospital unit that is not an intensive care unit. In another example, the non-critically ill hospitalized patient can be an outpatient recovering from a surgical procedure, but released from the post-anesthesia care unit. As such, the terms "non-critical ill" hospitalized patient and "non-ICU" hospitalized patient can be used interchangeably.

As used herein, the term "vital signs" can refer to a group of one or more medical characteristics that can be represented within one or more data streams. The data streams can, either individually or together, indicate a status of a patient's life-sustaining functions.

The "data streams" can refer to any means of carrying medical data relevant to the non-critically ill hospitalized patient to the remote monitoring location. For example, the vital signs can be reflected in one or more data streams pertaining to temperature, heart rate, respiratory rate, systolic blood pressure, diastolic blood pressure, heart rhythm, pulse oximetry, oxygen saturation, intracranial pressure, or the like. In another example, the data streams can pertain to patient motion, including acceleration, directionality, velocity or lack thereof, or the like. As a further example, the data streams can pertain to hemodynamic data, including central venous pressure, pulmonary arterial systolic, diastolic or mean arterial pressure, pulmonary capillary wedge pressure, left atrial pressure, left ventricular end diastolic pressure, left ventricular end diastolic volume, cardiac output as measured in liters per minute, or cardiac index as measured in liters per minute over body surface area, or the like. In another example, the data can be related to current or historical patient information derived from the electronic medical record, including current or prior medical conditions, family history including clinically relevant chromosomal abnormalities, or genetic polymorphisms, pharmacotherapy, current or prior surgery or non-surgical invasive medical procedures, or the like.

As used herein, the term "risk stratification" can refer to a process of medical decision making in which high risk or potentially high risk non-critically ill hospitalized patients are identified and their management prioritized. The risk stratification can be accomplished by a "risk score" representing a probability of a particular non-critically ill hospitalized patient determined based on data derived from one or more data streams.

As used herein, the term "patient census" can refer to the total number of non-critically ill hospitalized patients being monitored by a remote monitoring team.

As used herein, the term "remote monitoring team" can refer to a group of monitoring technicians, each working individually or a group working collaboratively as a team.

As used herein, the term "clinical status" can refer to a state or condition of a non-critically ill hospitalized patient. The clinical status can be represented by one or more vital signs or any other data stream parameters (e.g., related to motion sensor data).

As used herein, the term "acuity" can refer to the level of severity of an illness. For example, the non-critically ill hospitalized patient exhibiting the highest acuity characteristics can be prioritized.

As used herein, the term "vendor" can refer to a supplier of devices used for monitoring non-critically ill hospitalized patients. Examples of different vendors can include Philips, Siemens, General Electric, and the like.

As used herein, the term "patient" can refer to any warm-blooded organism (e.g., a person) receiving treatment for a medical condition as an inpatient. In some instances, the patient may be a non-critically ill hospitalized patient. For example, a non-critically ill patient can be any patient that is not being treated in a critical care unit like the intensive care unit (ICU).

As used herein, the term "hospital" can refer to any healthcare facility in which a non-critically ill hospitalized patient is receiving medical care as an inpatient or under observation status. The terms "care center" and "hospital" can be used interchangeably herein.

As used herein, the term "electronic medical record" (EMR) can refer to a digital version of a patient's medical chart. In some instances, the electronic medical record can be related to a particular patient encounter, which can be part of a larger electronic health record.

As used herein, the term "bedside team" can refer to one or more clinical providers associated with a particular patient. The bedside team can include practitioners, nurses, an emergency response team, and the like. The bedside team can include a wide range of personnel associated with the patient at the hospital, including patient care nursing assistants (PCNAs), nursing, physicians, respiratory therapists, physician assistants (PAs), certified nurse practitioners (CNPs), and the like.

II. Overview

The present disclosure relates generally to monitoring non-critically ill hospitalized patients from a remote location. For example, these non-critically ill patients still require hospital care, but not the critical care provided by an intensive care unit. More specifically, the present disclosure relates to systems and methods that employ a vendor-agnostic, risk stratified patient census with dynamic alerts to facilitate the remote monitoring of the non-critically ill hospitalized patients. Notably, the risk stratification can combat the problem of alarm fatigue, ensuring that the highest acuity patient alarms are prioritized to be handled preferentially, either by action (e.g., notifying appropriately-designed clinical personnel) or nullification. Additionally, the systems and methods can provide for streamlined paperless documentation of the encounter into the patient's electronic medical record.

The remote monitoring described herein represents a significant departure from traditional monitoring by either bedside personnel or remote monitoring technicians viewing data for a plurality of patients using monitors from a common vendor. With the patient plurality assigned to each vendor, discordance in the total census, or acuity of patients monitored, is common and the inability to re-distribute patients among vendors in an effort to balance the demands on monitoring personnel represents both a major problem and limitation. Traditional monitoring personnel and technicians can become overwhelmed by multiple simultaneous patient alarms without distinction of the clinical relevance of each alarm. Moreover, traditional monitoring personnel and technicians have a limited capacity for nullification of non-actionable alarms. The remote monitoring, as described herein, distributes the collective responsibility for monitoring a cohort of patients among a team, allows mixing and combination of patients using an aggregated data stream from different networks and vendors, provides a mechanism by which the highest acuity patient alarms are prioritized (or rearranged to a position of priority) on a display, provides a nullification mechanism for non-actionable alarms; and provides for a data exchange with the electronic medical record (EMR). Communication with bedside clinical providers is enabled through an electronic medical record data retrieval indicating name and contact information of providers, or through an electronic interface with a third party communication device provider.

III. Systems

One aspect of the present disclosure relates to remote monitoring of non-critically ill hospitalized patients, in which the positions of the various patients can be rearranged on a GUI 17 according to a calculated risk score for each of the patients. FIG. 1 illustrates a team approach (e.g., a team can include monitoring personnel or technicians T1-TM, where M is an integer greater than or equal to 2) for the remote monitoring of non-critically ill hospitalized patients from a plurality of different hospitals (e.g., hospital 1—hospital N, where N is an integer greater than or equal to 2) at a remote monitoring center 12 with one or more graphical user interfaces (GUI 17). Notably, the remote monitoring center 12 can accommodate hospitals 1-N 13-16 using different networks and monitoring equipment from different vendors.

Figure 2:
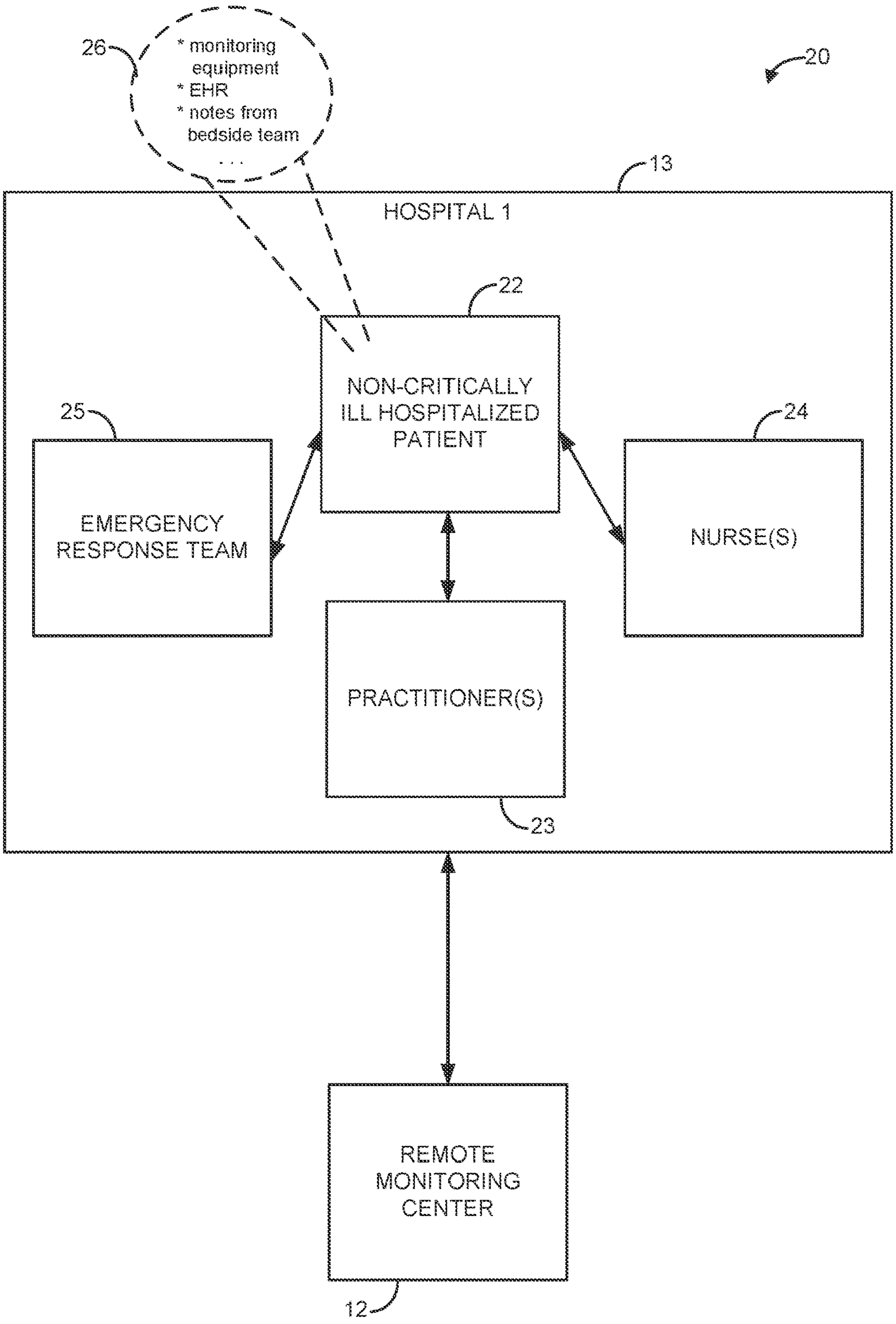
FIG. 2 is a block diagram showing types of information transfer within one of the plurality of different hospitals for one non-critically ill hospitalized patient.

FIG. 2 shows an example of the care team for a single non-critically ill hospitalized patient 22 at hospital 1 13. The care team can include a bedside team of hospital-based personnel and the monitoring team at the remote monitoring center 12. The bedside team can include a practitioner 23 (e.g., the admitting physician or licensed independent practitioner), the ward's nursing staff 24 (and other affiliated staff), and an emergency response team (e.g., an on call code team) 25 (and any additional hospital-based personnel). The nursing staff 24, the emergency response team 25, and the practitioner 23 responsible for the non-critically ill hospitalized patient can change throughout the day (e.g., with each changing shift, the coverage for the specific non-critically ill hospitalized patient can change). Similar bedside teams exist for other non-critically ill hospitalized patients, both at the same hospital or at different hospitals, but need not have the exact members illustrated in FIG. 2.

Communication can occur between the remote monitoring center 12 and each respective hospital 13-16. In some instances, the communication can be uni-directional. For example, data 26 related to a non-critically ill hospitalized patient 22 can be sent from hospital 1 13 to the remote monitoring center 12 as one or more data streams. In other instances, the communication can be bi-directional. As an example, data 26 related to a non-critically ill hospitalized patient 22 can be sent from hospital 1 13 to the remote monitoring center 12 as one or more data streams and the remote monitoring center 12 can send one or more notifications related to the non-critically ill hospitalized patient 22 to hospital 1 13 (e.g., to the bedside team, an entity related to the hospital, to the patient's EMR, or the like). In some instances, the communication can take place in connection with the GUI 17.

Using the example shown in FIG. 2, the remote monitoring center 12 can receive one or more data streams including data 26 associated with the non-critically ill hospitalized patient 22 from hospital 1 13. The data streams can be related to data 26 from monitoring equipment, EMRs, notes from the bedside team, or the like. For example, data streams from the monitoring equipment can include data related to one or more monitored vital signs. These data streams can be from different monitoring equipment using different protocols (e.g., from different vendors). As another example, the data streams from the monitoring equipment can include at least one alarm. The data streams can also include notes from the practitioner 23, the nursing staff 24, and/or the emergency response team 25. As another example, the data streams can come from or be associated with the non-critically ill hospitalized patient's EMR.

The remote monitoring center 12 can receive the one or more data streams and determine a risk score associated with the single non-critically ill hospitalized patient 22. For example, the risk score can indicate a clinical status or a change in a clinical status of the non-critically ill hospitalized patient. A patient census that includes patients being monitored by the remote monitoring center 12 can be displayed on one or more graphical user interfaces 17. In some instances, the patient census can include all of the patients being monitored by the remote monitoring center 12. In other instances, the remote monitoring center 12 can display a portion of the patients being monitored by the remote monitoring center 12 (e.g., each remote monitoring team can view a patient census that includes only the patients the team is monitoring). In still other instances, the patient census can include a master patient census with all of the patients being monitored by the remote monitoring center 12 and a focused (zoomed in) patient census focusing on a subset of the entire patient census.

Figure 3:
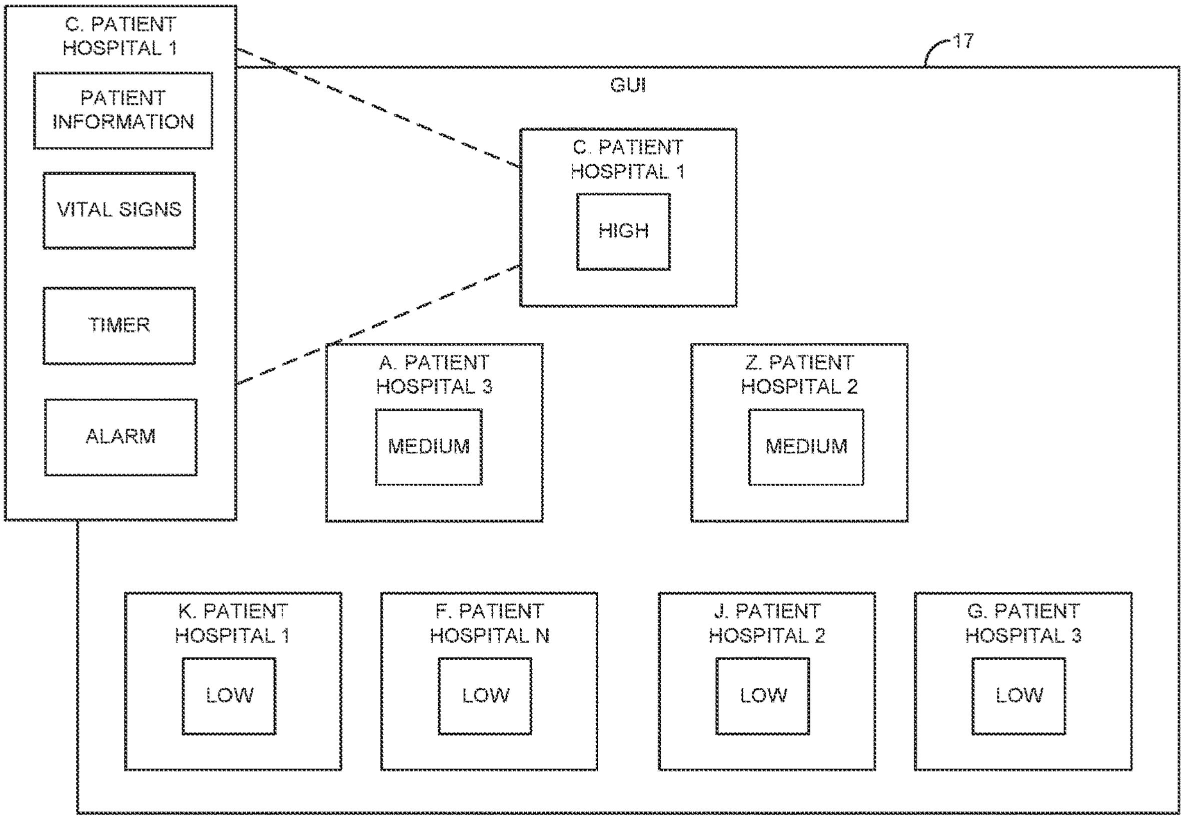
FIG. 3 is a schematic diagram showing an example risk stratified patient display in which the non-critically ill hospitalized patient with the highest risk score rises to the top of the screen.

An example of a patient census being displayed on a GUI 17 is shown in FIG. 3. The patient census can include a plurality of patients being monitored at a plurality of different hospitals, including:

- Hospital 1
  - K. Patient
  - C. Patient
- Hospital 2
  - Z. Patient
  - J. Patient
- Hospital 3
  - A. Patient
  - G. Patient
- Hospital N
  - F. Patient Each of the patients can be represented graphically (e.g., by an icon, a tile, or other graphical representation) on the GUI 17.

Each of the patients can be associated with a risk score (high, medium, low, as illustrated in FIG. 3). For example, the risk score can be related to a risk of the patient developing an actionable clinical event. This risk score can be calculated for each patient and the display configured based on the calculated risk scores.

Based on the calculated risk scores, the display shown in FIG. 3 can be risk stratified, such that the highest acuity patient is displayed most prominently. For example, C. Patient at Hospital 1, can have the highest determined risk score (e.g., "high") indicating the highest acuity and the highest likelihood of developing an actionable clinical event. Accordingly, C. Patient can be displayed the most prominently on the GUI 17. For example, C. Patient can be displayed in a different color, be displayed with an animation (e.g., blinking, shaking, or the like), be displayed zoomed in compared to the other patients, or the like. Patients with a "medium" risk score can have an elevated likelihood of developing an actionable clinical event—e.g., A. Patient at Hospital 3 and Z. Patient at Hospital 2. Patients with a "low" risk score can have small likelihood of developing an actionable clinical event, including: K. Patient at Hospital 1, F. Patient at Hospital N, J. Patient at Hospital 2, and G. Patient at Hospital 3. One way to distinguish these patients is color, with the high risk being red, the medium risk being yellow, and the low risk being green. However, the different risk levels can be distinguished in other ways (e.g., size, oscillatory movement, blinking, etc.). Moreover, the high, medium, and low risk scores can be relative to each other. For example, the highest risk score simply corresponds to the patient requiring the most immediate attention. In other instances, the high, medium, and low risk scores can be relative to one or more thresholds set by the remote monitoring center 12 (e.g., a patient with an alarm can be a high risk score, a patient with one or more vital sign potentially trending in the wrong direction could be a medium risk score, and a patient with normal vital signs and no alarms can be a low risk score). In some instances, the one or more thresholds can be set by an algorithm associated with the remote monitoring center 12. In other instances, the one of more thresholds can be set by the judgment of one or more technicians at the remote monitoring center 12. In still other instances, the one or more thresholds can be set according to a policy set for the remote monitoring center 12.

One or more technicians at the remote monitoring center 12 can select any one of the patients on the display and an expanded view of the patient will be displayed. For example, the highest acuity patient (like C. Patient at Hospital 1) can be selected, as illustrated in FIG. 3. The expanded view can include detailed information for the individual non-critically ill hospitalized patient (in some instances, structured based on the risk score). The detailed information, in some instances, can be set up to facilitate the discrimination of an actionable alarm and a non-actionable alarm. In some instances, the detailed view can include patient information, which can indicate one or more members of the bedside care team as responsible for the non-critically ill hospitalized patient. For example, with different shifts, different nurses and other staff members may be associated with the non-critically ill hospitalized patients. Technician(s) at the remote monitoring center 12 can alert the one or more members of the bedside care team of the risk score and/or any actionable alarm for the non-critical hospitalized patient (e.g., C. Patient). The patient information can also include information, such as room number, ward, physician, diagnosis, age, time monitored, and the like. In this example, the expanded view can also include information about one or more vital signs (at least a portion of which can be associated with the alarm), information about the alarm, and a timer (e.g., a quality assurance stopwatch timer), which can be used to gauge the time it take the remote monitoring center 12 to determine whether the alarm is actionable or non-actionable. For example, the timer can track the time since the patient was last viewed by a monitoring technician, track the time it takes the monitoring technician to view the alarm and eventually nullify the alarm, and the like, for data reporting and quality assurance purposes. Additionally, in some instances, at least a portion of the additional information can be displayed on the initial display with the patient icon or tile.

The GUI 17 display is altered by selection of the patient icon or tile with an expanded display for the individual patient inclusive of the following: 1) reason for the priority score-driven change in clinical status, 2) ECG waveform, 3) bedside monitoring vendor alarms history, 4) trended vitals data. A stopwatch timer commences from the closure of the patient tile after an expanded review to record the time since the tile was last selected. In some instances, results of the stopwatch timer can be reported to the EMR, the hospital, or any other agency monitoring the responsiveness of the remote monitoring center 12 and/or tracking clinical and quality outcomes.

As an example, the risk score can be calculated based on a sum of three individual components—a monitoring indication risk score derived based on a clinical event rate for a given monitoring indication, a vitals trending risk score based on at least two vital signs, and an alarms input risk score based on the clinical relevance of an alarm. A system 40 (FIG. 4) can include components that can be embodied on one or more computing devices that include a non-transitory memory 42 to store instructions and a processor 43 to facilitate execution of the instructions. In some instances, a receiver 44, a scorer 45 and/or an updater 47 can be stored as computer program instructions in the non-transitory memory 42 and executed by the processor 43. The processor 43 can be any type of device (e.g., a central processing unit, a microprocessor, or the like) that can facilitate the execution of the computer program instructions to determine the risk score. The non-transitory memory 42 can include one or more non-transitory medium (not a transitory signal) that can contain or store the program instructions for use by or in connection with matching patients with clinical trials by matching patient data to eligibility criteria. Examples (a non-exhaustive list) of non-transitory media can include: an electronic, magnetic, optical, electromagnetic, infrared, or semiconductor system, apparatus or device. More specific examples (a non-exhaustive list) of non-transitory media can include the following: a portable computer diskette; a random access memory; a read-only memory; an erasable programmable read-only memory (or Flash memory); and a portable compact disc read-only memory.

In this example, the system 40 can determine the risk score based on an input data stream 41 received by a receiver 44. It will be understood that the receiver 44 can receive data streams related to physiologic changes in each of the plurality of patients. The data stream 41 can be formatted according to a standard for transmission of clinical data, such as Health Level-7 (HL-7) or the like. The receiver 44 can be vendor agnostic, so the data stream 41 can be from any one of a number of vendors of monitoring equipment. The receiver 44 can mine the data (e.g., including at least two vital signs and an alarm) from the data stream 41 and send the data to the scorer 45 for calculation of the risk score 46, which can be used in the risk stratification of the GUI 17.

For example, the risk score 46 can be determined by the scorer 45 by summing a monitoring indication risk score (MIRS), a vitals trending risk score (VTRS), and an alarms input risk score (AIRS) (in other words, Risk Score=MIRS+VTRS+AIRS). The MIRS can be derived from an emergency response team (ERT) (e.g., emergency response team 25) event rate for a given monitoring indication (Xn=% ERT event rate for n/1.5) (e.g., syncope ERT event rate 4%; heart failure, acute ERT event rate 2%). The VTRS can be determined based on at least two vital signs from the data stream 41. The VTRS can be based on trends associated with the at least two vital signs (e.g., at least two of a systolic blood pressure, a diastolic blood pressure, a heart rate, a heart rhythm, a pulse oximetry, a respiratory rate, an oxygen saturation, and an intracranial pressure). The trends can be determined by comparing a current vital sign (Yc) to a moving average (Yma) of the vital sign over the last certain number of hours (e.g., 2 hours, 4 hours, 6 hours, etc.). For example, the moving average can be based on data stored in the non-transitory memory 42. The trends can be calculated for each key monitored vital sign. Any unmeasured parameter can drop out of the equation and carries no value. For example, VTRS can be calculated as a sum of the weighted difference between the current vital sign and the moving average of the vital sign scaled by a weighted monitoring constant specific to the vital sign. The AIRS can be determined based on a value assigned to the alarm triggered on the monitoring system (Zr). The value can be, for example, a numeric value (e.g., ranging from 50-200) based on a priority of the specific alarm. The priority can be derived based on a table that lists each alarm by vendor with a derived assigned value weighted based upon historical clinical outcomes data. For example, the assigned value can be derived based on historical data collected over time related to the alarms (e.g., the historical data can be stored in the non-transitory memory 42).

Figure 5:
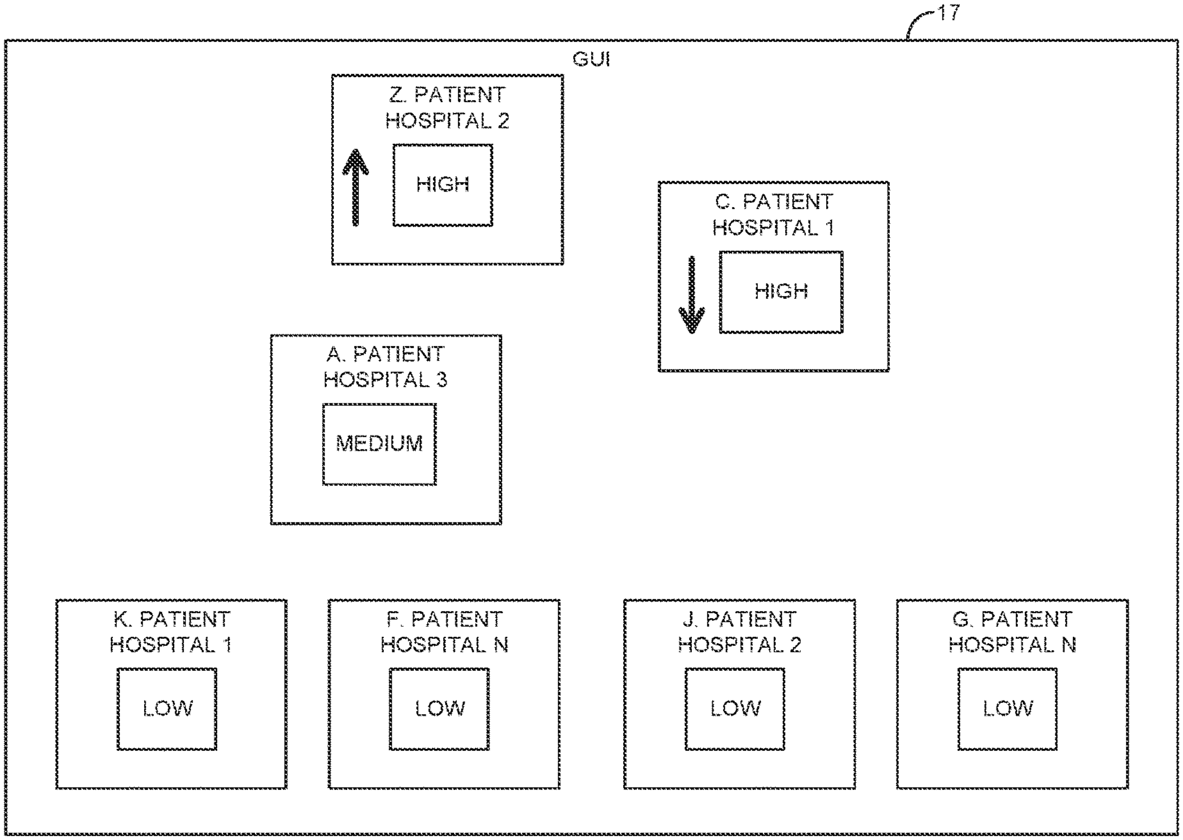
FIG. 5 is a schematic diagram showing the example risk stratified patient display shown in FIG. 3 after another patient is determined to exhibit a higher risk score.

The risk score can represent a probability of the particular patient developing an actionable clinical event. The updated risk score can be sent to the updater 47 to change the graphical representation of the clinical status of the plurality of patients (e.g., shown in FIG. 5) based on the determined risk score. As shown in FIG. 5, the risk score for Z. Patient at Hospital 2 has changed from yellow to red, indicating that Z. Patient at Hospital 2 now has a higher priority than C. Patient at Hospital 1. As shown in FIG. 5, the display of the patient census can be rearranged when a risk score for a patient increases, indicating a higher acuity for that particular patient. The higher acuity can be realized according to a dynamic alert that can be visualized on the GUI 17 by a change in the displayed clinical status. For example, the GUI 17 can be automatically refreshed and rearranged according to continuous updates by one or more real-time patient data streams.

The GUI 17 seen by the remote monitoring center 12, in some instances, can allow one or more technicians (T1-TM 18) at the remote monitoring center 12 interaction with updater 47. For example, the GUI 17 can provide one or more of the technicians with the ability to assess an alert and nullify the alert if deemed non-actionable. This interaction by the technicians with the GUI 17 is also available after identification and communication of an actionable clinical event. Communication with bedside clinical providers is enabled through electronic medical record data retrieval indicating name and contact information of providers, or through an electronic interface with a third party communication device provider. Once this communication has occurred, the technicians record an interaction with the updater 47 which nullifies this actionable clinical event's high risk graphical representation for a predetermined period of time (e.g. two to thirty minutes).

IV. Methods

Figure 6:
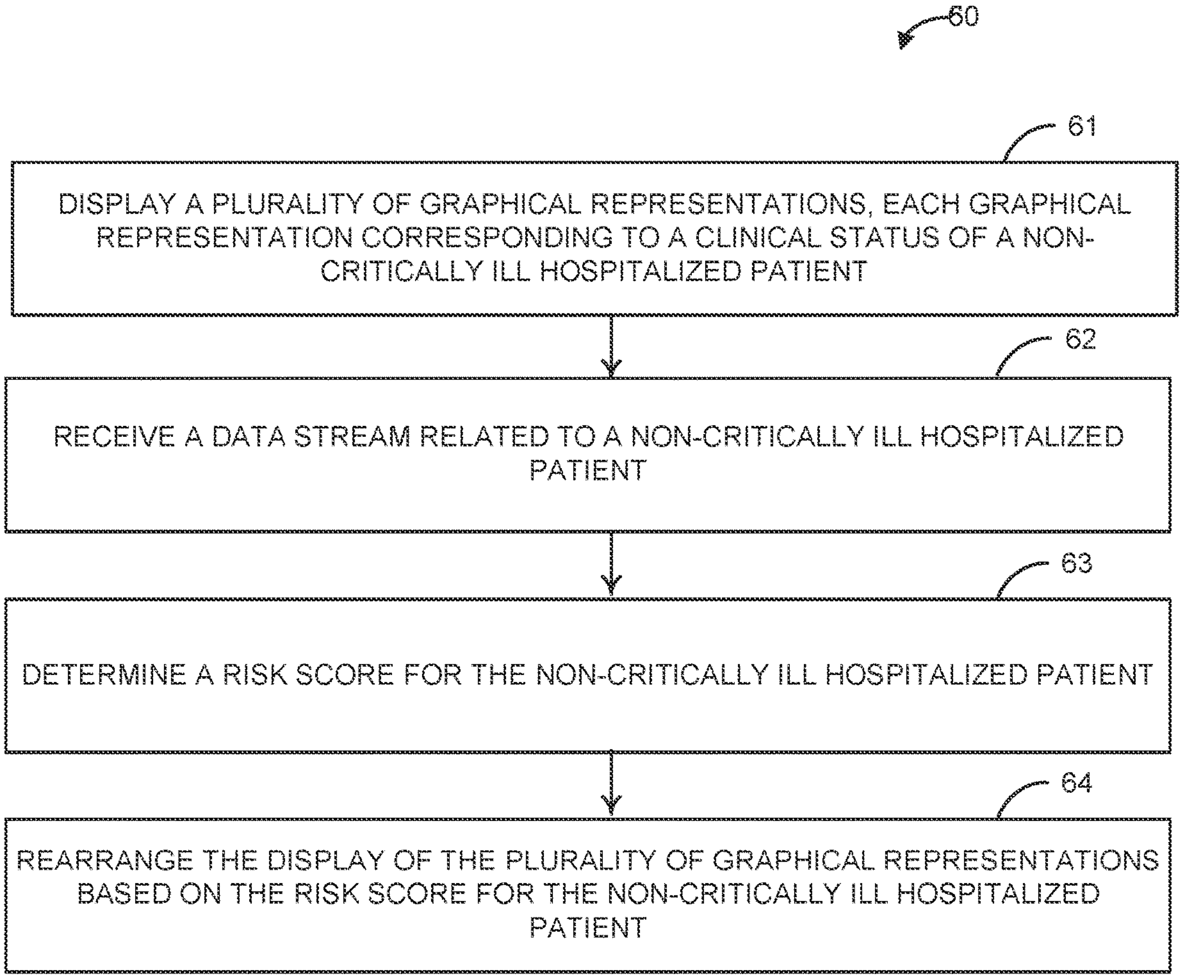
FIG. 6 is a process flow diagram illustrating a method for monitoring non-critically ill hospitalized patients from a remote location, in accordance with another aspect of the present disclosure.
Figure 7:
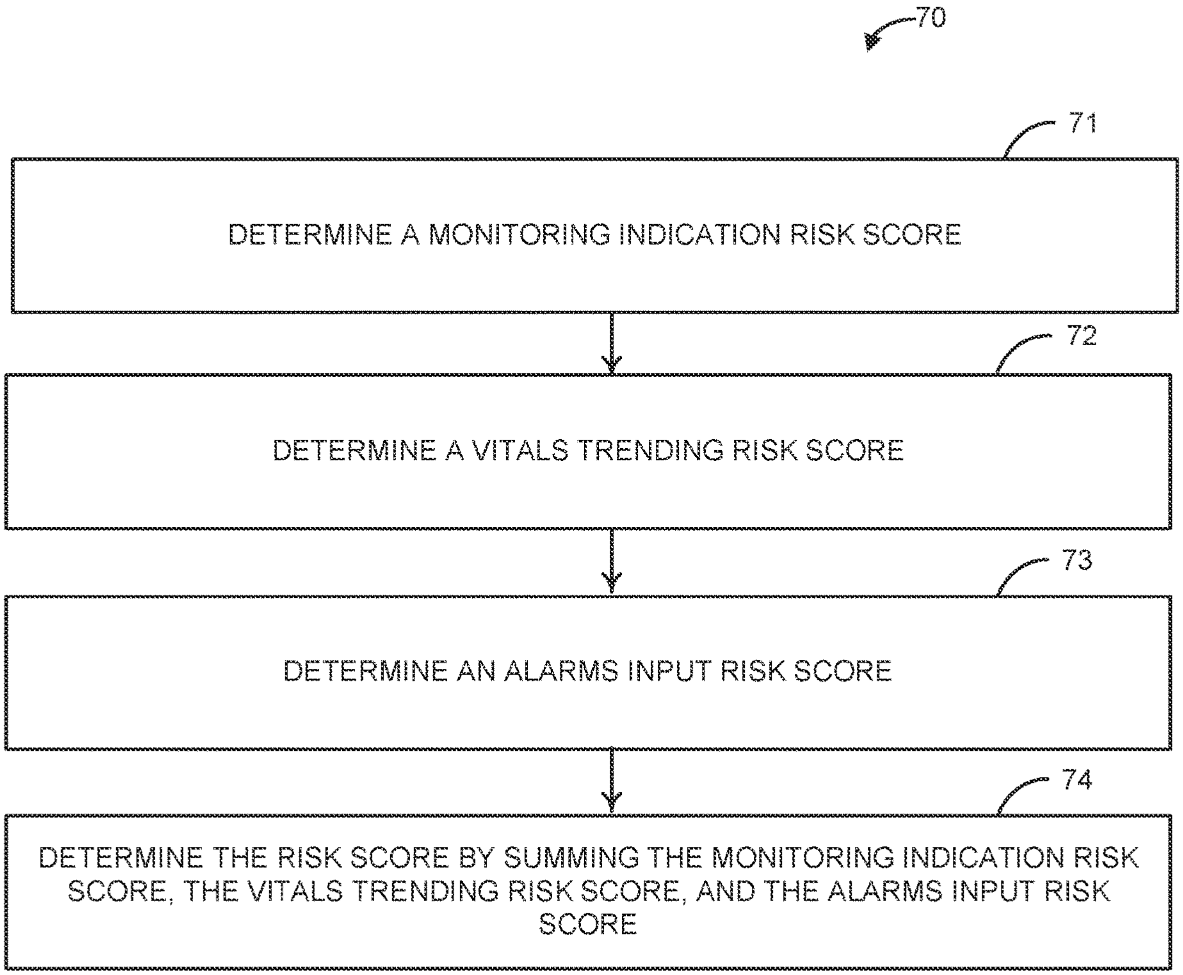
FIG. 7 is a process flow diagram illustrating a method for determining a risk score for a certain non-critically ill hospitalized patient that can be used in the method of FIG. 6.

Another aspect of the present disclosure can include a method 60 for monitoring patients from a remote location (FIG. 6). In some instances, the patients can be non-critical hospitalized patients from a plurality of different hospitals. The different hospitals can use monitoring devices from different vendors. The method 60 can be vendor agnostic, allowing inputs from each of the different monitoring devices from the different vendors. The monitoring of method 60 can provide a risk stratified patient census with dynamic alerts (e.g., as shown in the transition between FIG. 3 and FIG. 5) to enable the monitoring of the plurality of non-ICU patients. FIG. 7 shows an example of a method 70 for determining a risk score for a certain patient that can be used in the risk stratification of the method 60 shown in FIG. 6.

Figure 4:
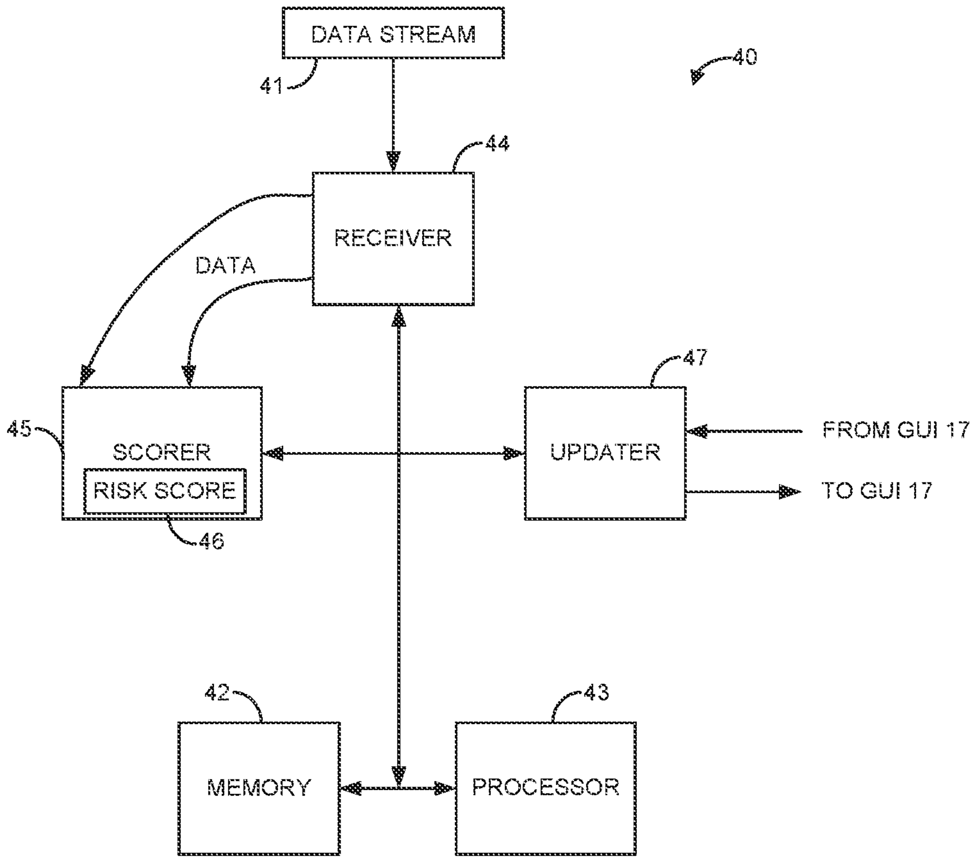
FIG. 4 is a block diagram showing a system that can monitor non-critically ill hospitalized patients from a remote location, according to an aspect of the present disclosure.

The methods 60 and 70 are illustrated as process flow diagrams with flowchart illustrations, which can be implemented by one or more components of the system 40, as shown in FIG. 4. For purposes of simplicity, the methods 60 and 70 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 60 and 70.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 60 and 70 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring now to FIG. 6, illustrated is a method 60 for monitoring non-critically ill hospitalized patients from a remote monitoring center (e.g., remote monitoring center 12) at a remote location. At 61, a graphical representation of a clinical status of a plurality of non-critically ill hospitalized patients (e.g., each of the plurality of non-critically ill hospitalized patients represented by tiles or icons, as shown in FIG. 3, with a clinical status for each of the plurality of non-critically ill hospitalized patients displayed in an easily perceivable way, such as in a certain color or oscillatory motion) can be displayed (e.g., at remote monitoring center 12). The graphical representation can be displayed on a graphical user interface (e.g., GUI 17) that can be viewed by a plurality of monitoring technicians (e.g., T1-TM 18) assigned to the plurality of non-critically ill hospitalized patients.

The remote monitoring center 12 can be linked to a plurality of hospitals (e.g., hospital 1— hospital N 13-16), which can potentially use monitoring devices from different vendors. At 62, a data stream (e.g., data stream 41) can be received (e.g., by receiver 44) from one of the hospitals related to at least one of the plurality of non-critically ill hospitalized patients. It will be understood that the remote monitoring center 12 can receive a plurality of data streams corresponding to different non-critically ill hospitalized patients from the different hospitals generated by machines from different vendors. The data streams can be formatted in accordance with a standard for transfer of clinical data, such as Health Level-7 (HL-7) or other data transmission standard. The receiver can process the data stream to retrieve or derive medical data (e.g., including at least two vital signs associated with the at least one non-critically ill hospitalized patient and an alarm triggered by a monitoring device associated with the at least one non-critically ill hospitalized patient). The medical data can be sent to a scorer (e.g., scorer 45), which, as 63, can determine a risk score for the at least one of the plurality of non-critically ill hospitalized patients based on the medical data. The risk score can represent a probability of the at least one of the plurality of non-critically ill hospitalized patients developing an actionable clinical event. The updated risk score can be sent to an updater (e.g., updater 47), which can, at 64, change the graphical representation of the clinical status of the plurality of non-critically ill hospitalized patients (e.g., shown in FIG. 5) based on the determined risk score.

For example, a second data stream, which can be from a different vendor, can be received. The second data stream can be related to another at least one of the plurality of non-critically ill hospitalized patients. Another risk score can be determined for the another at least one of the plurality of non-critically ill hospitalized patients based on medical data derived from the another data stream. The graphical representation of the clinical status can be changed (e.g., issuing a dynamic alert) to illustrate the newly calculated another risk score. When the another risk score illustrates that the another non-critically ill hospitalized patient has a risk score that is higher than any other of the plurality non-critically ill hospitalized patients, the GUI 17 can be dynamically updated to illustrate the another of the plurality of non-critically ill hospitalized patients in a more prominent position, indicating the higher risk score.

FIG. 7 illustrates a method 70 for determining a risk score for a certain non-critically ill hospitalized patient that can be used in the risk stratification. For example, the risk score of FIG. 6 can be determined by the scorer (e.g., scorer 45) according to the method 70. At 71, a monitoring indication risk score (MIRS) can be determined. For example, the MIRS can be derived from an event rate for a given monitoring indication (Xn=% ERT event rate for n/1.5). At 72, a vitals trending risk score (VTRS) can be determined based on at least two vital signs from the data stream. The VTRS can be based on trends associated with the at least two vital signs (e.g., at least two of a systolic blood pressure, a diastolic blood pressure, a heart rate, a heart rhythm, a pulse oximetry, a respiratory rate, an oxygen saturation, or an intracranial pressure). The trends can be determined by comparing a current vital sign (Yc) to a moving average (Yma) of the vital sign over the last certain number of hours (e.g., 2 hours, 4 hours, 6 hours, 8 hours, 12 hours, or the like). The trends can be calculated for each key monitored vital sign. Any unmeasured parameter can drop out of the equation and carries no value. For example, VTRS can be calculated as a sum of the weighted difference between the current vital sign and the moving average of the vital sign scaled by a weighted monitoring constant specific to the vital sign (e.g., an integer value greater than 2, in some instances from 5 to 300). At 73, an alarms input risk score (AIRS) can be determined. A value can be assigned to the alarm triggered on the monitoring system (Zr). The value can be, for example, a numeric value (e.g., ranging from 5-100) based on a priority of the specific alarm. The priority can be derived based on a table that lists each alarm by vendor with a derived assigned value. For example, the assigned value can be derived based on historical data collected over time related to the alarms. At 74, the risk score can be determined by summing the MIRS, the VTRS, and the AIRS (Risk Score=MIRS+VTRS+AIRS).

The risk score can be used according to the following example. A central monitoring station of the remote monitoring center can include a graphical user interface (e.g., GUI 17) that can display a patient census with an associated, readily-discernible clinical status for each non-critically ill hospitalized patient. The GUI corresponding to the plurality of non-critically ill hospitalized patients can be monitored by a small group of technicians working together to provide team-based monitoring with notifications to bedside clinical providers. Detailed data for the patient can be viewed by selecting the patient tile or icon. The GUI display is based on determined risks of each of the patients developing an actionable clinical event. The risks can be quantified as a Priority Risk Score (or "risk score"), which is calculated based on a sum of three individual components—a monitoring indication risk score, a vitals trending risk score based on at least two vital signs, and an alarms input risk score based on the clinical relevance of an alarm. The display of the patient census can change when a risk score for a patient increases, indicating a higher acuity for the patient. The higher acuity can be realized according to a dynamic alert that can be visualized on the GUI by a change in the displayed clinical status. The application of color and oscillatory motion to the patient tile or icon visually represents a change in clinical status on the display. A stopwatch timer commences from the onset of change in clinical status until the tile is selected for expanded review by the monitoring technician. The timer variable can be used for quality assurance purposes, or for tracking of clinical outcomes. The expanded view provides detailed information for the individual patient as structured by the risk score to facilitate the discrimination of an actionable alarm and nullification of a non-actionable alarm.

V. Examples

The following Examples show the operation of the system shown in FIGS. 1-5 in the case of a hypothetical high risk patient, low risk patient, and moderate risk patient.

High Risk Patient Scenario

A new patient (Patient H) is admitted to Hospital 1 13 with a high-risk indication for telemetry order in the associated electronic medical record (EMR). The telemetry order is communicated to nursing 24 and monitoring technicians 18 at a remote monitoring center 12. The telemetry order is also accessible to all practitioners 23 in addition to the emergency response team 25 at Hospital 1 13. A graphical user interface (GUI) 17 at the remote monitoring center 12 associated with the technicians is updated with a representation of Patient H (e.g., a tile or icon view and an expanded view as described above).

Upon application of one or more monitoring devices to Patient H at Hospital 1 13, the representation of Patient H on the GUI 17 is updated to indicate, by color: a monitoring indication risk score 71, a vitals trending risk score 72, and an alarms input risk score 73. For Patient H, this includes a high risk indication, stable vital signs, and no monitoring alarms, leading to an initial risk score 74 of "low". The representation of Patient H on the GUI can be configured as "low risk". However, Patient H can experience a significant change to the vital signs and multiple monitor alarms, which change the risk score 74 from "low" to "high". The changes to the vital signs and the multiple monitor alarms are received via data streams 41 to the receiver 44. The receiver 44 sends the data streams 41 to the scorer 45, which determines a risk score 46 based on the combination of the telemetry indication (monitoring indication, the vital signs, and the monitor alarms). The scorer 45 sends the risk score and the updated data to the updater 47, which updates the GUI 17 to reflect the "high risk" of Patient H (e.g., a color change and/or oscillatory motion).

Due to the "high" risk score, Patient H rises to the top of the screen of the GUI 17. The change in the GUI 17 triggers a response from one or more of the monitoring technicians 18. The response can be communicating with the bedside nursing personnel 24 and/or the emergency response team 25 regarding the significant change. The bedside nursing personnel 24 and/or the emergency response team 25 can interact with Patient H to provide resuscitative or supportive measures, as needed. The monitoring technician interacts with the updater 47 through the GUI 17 to indicate a change in the status of this actionable alarm. The updater 47 transmits this data to the scorer 45 to generate an updated risk score 46, which can flow back through the updater 47 to reflect a temporarily lower score on the GUI 17 (e.g., medium or high, but lower acuity). The temporarily lower score is based on the communication notifying the care team of Patient H's change. If the care team cancel the alarm and/or cause a change in the vital signs, the risk score can return to "low risk" and the representation of Patient H on the GUI 17 can return to the lower portion of the GUI 17.

Low-Risk Patient Scenario

Patient L is admitted to Hospital 2 14 with a low-risk indication for telemetry order in the electronic medical record. The order is communicated via EMR to nursing 24 and monitoring technicians 18 at remote monitoring center 12. The telemetry order is also accessible to all practitioners 23 in addition to the emergency response team 25 at Hospital 2. A graphical user interface (GUI) 17 at the remote monitoring center 12 associated with the technicians is updated with a representation of Patient L (e.g., an tile or icon view and an expanded view as described above).

Upon application of one or more monitoring devices to Patient L, the representation of Patient L on the GUI 17 is updated to indicate, by color: a monitoring indication risk score 71, a vitals trending risk score 72, and an alarms input risk score 73. For Patient L, this includes a low risk indication, stable vital signs, and no monitoring alarms, leading to an initial risk score 74 of "low". This GUI 17 is viewed by a team of monitoring technicians 18 at the remote monitoring center 12. This team is also monitoring patients from Hospital 1 13, Hospital 3 15, and Hospital N 16 on their risk stratified patient display (shown, for example, in FIG. 3).

During Patient L's time on the monitoring system, there are no significant changes requiring intervention from the remote monitoring center 12. Upon discharge, this patient's monitoring equipment is removed and information is discharged from the monitoring system, thus removing the icon representing Patient L from the GUI 17 visible to the remote monitoring center 12. The patient's EMR can be updated with information regarding the discharge.

Moderate-Risk Patient Scenario

Patient M is admitted to Hospital 2 14 with a low risk indication for telemetry order in the electronic medical record. The order is communicated via EMR to nursing 24 and monitoring technicians 18 at the remote monitoring center 12. The telemetry order is also accessible to all practitioners 23 in addition to the emergency response team 25 at Hospital 2. A graphical user interface (GUI) 17 at the remote monitoring center 12 associated with the technicians is updated with a representation of Patient M (e.g., a tile or icon view and an expanded view as described above).

Upon application of one or more monitoring devices, the representation of Patient M on the GUI 17 is updated to indicate, by color: a monitoring indication risk score 71, a vitals trending risk score 72, and an alarms input risk score 73. For Patient M, this includes a low risk indication, stable vital signs, and no monitoring alarms, leading to an initial risk score 74 of "low". However, Patient M can experience a significant change to the vital signs and multiple monitor alarms, which change the risk score 74 from "low" to "moderate". The changes to the vital signs and the multiple monitor alarms are received via data streams 41 to the receiver 44. The receiver 44 sends the data streams 41 to the scorer 45, which determines a risk score 46 based on the combination of the telemetry indication (monitoring indication), the vital signs, and the monitor alarms. The scorer 45 sends the risk score and the updated data to the updater 47, which updates the GUI 17 to reflect the "moderate risk" of Patient M (e.g., a color change and/or oscillatory motion).

During Patient M's time on the monitoring system, Patient M experiences a change in vital signs resulting in Patient M's overall level of risk moving from "low" to "moderate". These changes are received via data stream 41 to the receiver 44. The receiver 44 sends this data stream 41 to the scorer 45, which determines a risk score 46 based on the combination of the telemetry indication, vital signs, and monitor alarms. The scorer 45 then sends the updated risk score and/or the data to the updater 47, which updates the GUI 17 to reflect a color change and/or oscillatory motion of Patient M's representation.

With a moderate level of overall risk, Patient M rises to the middle of the screen. The GUI 17 change triggers a response from the monitoring technicians 18 at the remote monitoring center 12. For example, one or more monitoring technicians will review the patient's now moderate risk score 46 and associated vitals trending risk score 72 to determine if the moderate risk score is actionable. After review, changes are determined to be non-actionable and nullified in the updater 47 through the GUI 17, which indicates the change in the status of this non-actionable alarm. For example, the indication of the non-actionable alarm can be an indication taken by the monitoring technician, such as actively selecting an "alarm nullify" indication on the GUI 17. The nullification can be updated to the EMR. The updater 47 transmits this data to the scorer 45 to generate an updated risk score 46, which flows back through the updater 47 to reflect a temporary lower score on the GUI 17. This new score is based on the review by the monitoring technician. Once Patient M has a lower score the icon representing Patient M on the GUI 17 returns to the lower portion of the risk stratified patient display (shown in FIG. 3). Upon discharge, this patient's monitoring equipment is removed and information is discharged from the monitoring system, thus removing the representation on the GUI 17 visible to the remote monitoring center 12.

From the above description, those skilled in the art will perceive improvements, changes and modifications. Such improvements, changes and modifications are within the skill of one in the art and are intended to be covered by the appended claims.

What is claimed is:

1. A system comprising:

at least one piece of monitoring equipment located at each of a plurality of hospitals, each of the plurality of hospitals having at least one patient requiring monitoring by the at least one piece of monitoring equipment, wherein each of the at least one piece of monitoring equipment located at each of the plurality of hospitals has different data stream protocols corresponding to a vendor;

a network connected to each of the at least one piece of monitoring equipment; and a remote monitoring center, physically remote from each of the plurality of hospitals, configured to monitor each of the patients requiring monitoring at each of the plurality of hospitals and connected to the network with each of the plurality of hospitals, wherein the remote monitoring center comprises:

at least one graphical user interface (GUI) configured to simultaneously display graphical representations corresponding to each of the patients requiring monitoring; and a computing device linked to the GUI comprising:

a memory storing computer executable instructions; and a processor coupled to the memory and configured to execute the computer executable instructions to at least:

receive a data stream associated with each of the patients requiring monitoring from the network of each of the plurality of hospitals in real time, wherein each of the data streams are transmitted according to the different data stream protocols and comprises at least one vital sign for each of the patients requiring monitoring, at least one alarm data of the at least one piece of monitoring equipment, and electronic medical record data, wherein the processor is agnostic to the different data stream protocols;

determine a risk score associated with each of the patients requiring monitoring based on the data stream at a given time;

categorize the risk scores for each of the patients requiring monitoring based on acuity at the given time; and alter the graphical representations corresponding to each of the patients requiring monitoring on the GUI to more prominently display the graphical representation of each of the patients requiring monitoring having the most acute risk scores at the given time compared to the graphical representations of each of the patients requiring monitoring having less than the most acute risk scores, wherein the GUI is continuously refreshed based on the data stream, wherein more prominently is at least one of automatically changing a color of, animated motion of, or zooming in on the graphical representation of each of the patients requiring monitoring having the most acute risk scores at the given time while still showing the graphical representations of each of the patients requiring monitoring.

2. The system of claim 1, wherein when the processor is further configured to send an alert to one or more members of a bedside care team associated with each of the patients requiring monitoring having the most acute risk scores.

3. The system of claim 1, wherein the processor is further configured to categorize the risk scores into a high category, a medium category, or a low category based on the acuity.

4. The system of claim 1, wherein the GUI is a part of a central monitoring station at the remote monitoring center.

5. The system of claim 1, wherein the graphical representations of each of the patients requiring monitoring comprise a display of a clinical status for each of the patients requiring monitoring.

6. The system of claim 1, wherein the graphical representations of each of the patients requiring monitoring is selectable, wherein when one of the graphical representations is selected the processor is further configured to alter the GUI to display detailed data related to that patient of the one of the graphical representations.

7. The system of claim 6, wherein the detailed data related that patient comprises at least one of: one or more parameters triggering the risk score for that patient, real-time ECG waveform data, stored alarmed ECG data, bedside monitoring vendor alarms history, trended vitals data, or a communication link to a bedside clinical provider.

8. The system of claim 7, wherein the detailed data is shown in a detailed view of the graphical representation that is displayed upon selection of the graphical representation.

9. The system of claim 6, wherein the processor quantifies a responsiveness of the monitoring technician based on a time to view the detailed data of the graphical representation corresponding to each of the patients requiring monitoring having the most acute risk scores at the given time.

10. The system of claim 1, wherein the processor links each graphical representation corresponding to each patient requiring monitoring to an electronic health record associated with each of the patients requiring monitoring.

11. The system of claim 1, wherein the data stream further comprises at least two vital signs and an alarm from one of the at least one piece of monitoring equipment connected to each patient requiring monitoring.

12. The system of claim 11, wherein the risk scores of each of the patients requiring monitoring are determined by summing at least a vitals trending risk score determined based on values associated with the at least two vital signs and an alarm input risk score determined based on a value a vendor of the at least one piece of monitoring equipment connected to each patient requiring monitoring assigned to the alarm.

13. The system of claim 1, wherein the risk scores indicate a likelihood of each of the patients requiring monitoring developing an actionable clinical event.

14. A method comprising:

receiving, by a processor associated with a remote monitoring center, a data stream associated with each patient requiring monitoring from a network connected to a plurality of hospitals in real time, wherein each of the plurality of hospitals comprise at least one piece of monitoring equipment associated with at least one of the each patients requiring monitoring and each of the at least one piece of monitoring equipment have different data stream protocols corresponding to a vendor, wherein the processor is agnostic to the different data stream protocols, and wherein the remote monitoring center is physically remote from the plurality of hospitals;

determining, by the processor, risk scores associated with each patient requiring monitoring based on the data stream at a given time; and categorizing, by the processor, the risk scores for each of the patients requiring monitoring based on acuity at the given time;

displaying, by the processor, graphical representations corresponding to each of the patients requiring monitoring on a graphical user interface (GUI) at the remote monitoring center simultaneously; and rearranging, by the processor, the GUI at the given time to more prominently display the graphical representations representing patients requiring monitoring with a new higher risk score above the graphical representations of each of the patients requiring monitoring having less acute risk scores and to at least one of automatically change a color of, animated motion of, or zoom in on the graphical representations of each of the patients requiring monitoring with the new higher risk score.

15. The method of claim 14, further comprising sending, by the processor, an alert to one or more members of a bedside care team associated with each of the patients requiring monitoring having the most acute risk scores.

16. The method of claim 14, wherein the data stream comprises at least two vital signs and an alarm from one piece of monitoring equipment connected to each patient requiring monitoring.

17. The method of claim 16, wherein the determining the risk scores of each of the patients requiring monitoring further comprises summing at least a vitals trending risk score determined based on values associated with the at least two vital signs and an alarm input risk score determined based on a value a vendor of the at least one piece of monitoring equipment connected to each patient requiring monitoring assigned to the alarm.

18. The method of claim 14, further comprising displaying, by the processor, a general view of the graphical representation comprising a clinical status; and upon receiving a selection of a portion of the general view, displaying, by the processor, a detailed view comprising parameters corresponding to the clinical status.

19. The method of claim 18, further comprising quantifying, by the processor, a responsiveness of the monitoring technician based on a time to view a detailed view of the graphical representation corresponding to each of the patients requiring monitoring having the most acute risk scores at the given time.

20. The method of claim 18, wherein each graphical representation is linked to an electronic health record associated with a respective patient.

* * * * *